United States Patent
Vaez-Iravani et al.

(10) Patent No.: US 9,568,435 B2
(45) Date of Patent: *Feb. 14, 2017

(54) SIMULTANEOUS MULTI-SPOT INSPECTION AND IMAGING

(71) Applicant: KLA-Tencor Corporation, Milpitas, CA (US)

(72) Inventors: Mehdi Vaez-Iravani, Los Gatos, CA (US); Lawrence Robert Miller, El Macero, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/465,656

(22) Filed: Aug. 21, 2014

(65) Prior Publication Data

US 2014/0362372 A1 Dec. 11, 2014

Related U.S. Application Data

(63) Continuation of application No. 12/362,191, filed on Jan. 29, 2009, now Pat. No. 8,817,248, which is a
(Continued)

(51) Int. Cl.
*G01N 21/00* (2006.01)
*G01N 21/88* (2006.01)
(Continued)

(52) U.S. Cl.
CPC ...... *G01N 21/8806* (2013.01); *G01N 21/9501* (2013.01); *G01N 21/95623* (2013.01);
(Continued)

(58) Field of Classification Search
USPC ........................................... 356/237.1–237.5
See application file for complete search history.

(56) References Cited

U.S. PATENT DOCUMENTS 4,247,203 A 1/1981 Levy et al.
4,464,050 A * 8/1984 Kato et al. .................. 356/239.1
(Continued)

FOREIGN PATENT DOCUMENTS

EP 0 266 728 11/1987
JP 9015163 1/1997
WO WO 03/089872 A3 10/2003

OTHER PUBLICATIONS

S. Stokowski and M. Vaez-Iravani, "Wafer Inspection Technology Challenges for ULSI Technology", Proceedings of Conference on Characterization and Metrology for ULSI Technology, Edited by D.G. Seiler, A. C. Diebold, W. M. Bullis, T. J. Shaffner. R. McDonald, and E.J. Walters, American Institute of Physics, pp. 405-415 (1998).

(Continued)

*Primary Examiner* — Tri T Ton
(74) *Attorney, Agent, or Firm* — Kwan & Olynick LLP (57) ABSTRACT

A compact and versatile multi-spot inspection imaging system employs an objective for focusing an array of radiation beams to a surface and a second reflective or refractive objective having a large numerical aperture for collecting scattered radiation from the array of illuminated spots. The scattered radiation from each illuminated spot is focused to a corresponding optical fiber channel so that information about a scattering may be conveyed to a corresponding detector in a remote detector array for processing. In one embodiment, a one-dimensional array of illumination beams is directed at an oblique angle to the surface to illuminate a line of illuminated spots at an angle to the plane of incidence. Radiation scattered from the spots are collected along directions perpendicular to the line of spots or in a double dark field configuration.

17 Claims, 5 Drawing Sheets

Related U.S. Application Data continuation of application No. 11/553,174, filed on Oct. 26, 2006, now Pat. No. 7,492,451, which is a continuation of application No. 10/418,352, filed on Apr. 17, 2003, now Pat. No. 7,130,039, which is a continuation-in-part of application No. 10/125,906, filed on Apr. 18, 2002, now abandoned.

(51) Int. Cl.
  *G01N 21/956* (2006.01)
  *G01N 21/95* (2006.01)
(52) U.S. Cl.
  CPC ............... *G01N 2021/8822* (2013.01); *G01N 2021/8845* (2013.01); *G01N 2201/12* (2013.01)

(56) References Cited

U.S. PATENT DOCUMENTS

| | | | |
|---|---|---|---|
| 4,579,455 A | 4/1986 | Levy et al. |
| 4,629,319 A | 12/1986 | Clarke et al. |
| 4,831,274 A | 5/1989 | Kohno et al. |
| 4,898,471 A | 2/1990 | Vaught et al. |
| 4,974,927 A | 12/1990 | Kimura |
| 5,192,856 A | 3/1993 | Schaham |
| 5,206,699 A | 4/1993 | Stewart et al. |
| 5,251,010 A | 10/1993 | Maltby, Jr. |
| 5,274,434 A | 12/1993 | Morioka et al. |
| 5,289,260 A | 2/1994 | Miyazaki et al. |
| 5,463,459 A | 10/1995 | Mrioka et al. |
| 5,479,259 A | 12/1995 | Nakata et al. |
| 5,528,360 A | 6/1996 | Kohno |
| 5,530,550 A | 6/1996 | Nikoonahad et al. |
| 5,576,831 A | 11/1996 | Nikoonahad et al. |
| 5,585,916 A | 12/1996 | Miura et al. |
| 5,644,393 A | 7/1997 | Nakamura et al. |
| 5,719,840 A | 2/1998 | Jann |
| 5,737,074 A | 4/1998 | Haga et al. |
| 5,748,305 A | 5/1998 | Shimono et al. |
| 5,864,394 A | 1/1999 | Jordan et al. |
| 5,883,710 A | 3/1999 | Nikoonahad et al. |
| 5,917,797 A | 6/1999 | Kosoburd |
| 5,965,896 A | 10/1999 | Marton |
| 6,081,325 A | 6/2000 | Leslie et al. |
| 6,208,411 B1 | 3/2001 | Vaez-Iravani |
| 6,369,886 B2 | 4/2002 | Ishikawa et al. |
| 6,538,730 B2 | 3/2003 | Vaez-iravani et al. |
| 6,608,676 B1 | 8/2003 | Zhao et al. |
| 6,643,007 B2 | 11/2003 | Le |
| 6,671,042 B1 * | 12/2003 | Almogy | 356/237.3 |
| 6,781,686 B2 | 8/2004 | Hunt |
| 6,858,859 B2 | 2/2005 | Kusunose |
| 6,861,660 B2 | 3/2005 | Almogy et al. |
| 7,088,443 B2 | 8/2006 | Vaez-Iravani et al. |
| 7,130,039 B2 | 10/2006 | Vaez-Iravani et al. |
| 2003/0085335 A1 * | 5/2003 | Almogy et al. ........ | 250/208.1 |
| 2009/0161096 A1 * | 6/2009 | Vaez-Iravani et al. .... | 356/237.2 |

OTHER PUBLICATIONS

"Notification of the Transmittal of the International Search Report or the Declaration" corresponding to PCT/US03/12070, filed Apr. 18, 2003, 4 pages.

"Numerical Aperture and Resolution," http://www.gonda.ucla.edu/bri_core/na.htm, Apr. 4, 2006, 2 pages.

Gara, "Automatic Microcircuit and Wafer Inspection in Electronics Test," May 1981, pp. 60-70.

* cited by examiner

SIMULTANEOUS MULTI-SPOT INSPECTION AND IMAGING

CROSS-REFERENCE TO RELATED APPLICATIONS

This application is a continuation of application Ser. No. 12/362,191, filed Jan. 29, 2009, which is a continuation of Ser. No. 11/553,174, filed Oct. 26, 2006, now U.S. Pat. No. 7,492,451, which is a continuation of application Ser. No. 10/418,352, filed Apr. 17, 2003, now U.S. Pat. No. 7,130,039; which application is a continuation-in-part of application Ser. No. 10/125,906, filed Apr. 18, 2002, now abandoned, and which also claims the benefit of Provisional Application No. 60/426,577, filed Nov. 15, 2002. These applications are incorporated herein in their entirety by reference as if fully set forth herein.

BACKGROUND OF THE INVENTION

This invention relates in general to the inspection of surfaces to detect anomalies, and in particular, to an improved system that illuminates the surface inspected at the plurality of spots simultaneously for anomaly detection.

Conventional optical inspection methods employing scanning techniques typically causes a single spot on the surface inspected to be illuminated where the spot is scanned over the entire surface for anomaly detection. For improved signal-to-noise ratio caused by background scattering, the size of the illuminated spot has been continually reduced. This means that the amount of time required for the spot to scan over the entire surface is increased which is undesirable.

One solution to the above dilemma is proposed in U.S. Pat. No. 6,208,411, which is incorporated herein by reference in its entirety. This patent proposes a massively parallel inspection and imaging system which illuminates the surface at a plurality of spots where scattered light from the spots are imaged onto corresponding detectors in a detector array.

While the system in U.S. Pat. No. 6,208,411 provides a major enhancement in the total inspection throughput, it may be further improved for enhanced performance in certain applications. It is, therefore, desirable to provide an improved multi-spot inspection and imaging system with enhanced characteristics.

SUMMARY OF THE INVENTION

While the system described in U.S. Pat. No. 6,208,411 provides a major enhancement in the total inspection throughput, for some applications, it may be desirable for the system to be compact and have a smaller footprint. In such event, it may be desirable for the focusing optics focusing multiple beams of radiation to an array of spots and the imaging optics imaging scattered radiation from the spots to an array of receivers or detectors to employ different objectives. In one embodiment of the invention, the objective used for imaging has a larger numerical aperture than the objective use for focusing. This enhances detection sensitivity.

In another embodiment, radiation reflected from an array of illuminated spots on the surface may be imaged onto a first array of receivers or detectors in a bright field detection configuration and radiation scattered from the spots may be imaged onto a second array of receivers or detectors in a dark field detection configuration. The use of both bright and dark field detection provides more information for anomaly detection.

In yet another embodiment, the multiple beams of radiation are focused to an array of spots on the surface where the radiation comprises at least one wavelength component in the ultraviolet ("UV") or deep ultraviolet range of wavelengths. Scattered or reflected radiation from the spots are imaged by means of optics that comprises a reflective objective to reduce chromatic aberration.

In still another embodiment in a compact and modular approach, an optical head for anomaly detection includes illumination optics focusing illumination beams of radiation to an array of spots on a surface and imaging optics that images scattered or reflected radiation from the spots onto an array of optical fibers. Each of the fibers contains scattered or reflected radiation from one of the spots. Such light may be supplied to detectors outside the optical head for processing and anomaly detection. Instead of optical fibers coupled to detectors, other types of receivers may also be used.

In still another embodiment of the invention, in addition to the optical head described immediately above, a plurality of detectors generate signals in response to radiation scattered or reflected by the surface or radiation from the fibers and rotational motion is caused between the surface and the illumination beams so that the beams are scanned over substantially the entire area of the surface. Where the surface inspected is that of a semiconductor sample having multiple dice thereon, signals from the detectors from at least two dice or portions thereof of the surface are stored as the beams are scanned over the surface. Preferably, the scattered radiation from the two dice may be compared in a die-to-die comparison for anomaly detection.

The surface inspected sometimes has diffraction patterns thereon. In such event, scattered or reflected radiation from the array of illuminated spots on the surface may be masked by diffraction from the pattern. Thus, in another embodiment of the invention, when relative rotational motion is caused between the surface inspected and the illumination beams, a spatial filter in or near the focal plane of the imaging objective having an aperture that is caused to move substantially in synchronism with the rotational motion to reduce diffraction from the pattern that is passed to the array of receivers or detectors. Alternatively, as rotational motion is caused between the surface and the beams, a stationary filter in the shape of an annular aperture may be employed to shield the detectors from pattern diffraction. For some applications, both types of filters may be used at the same time during inspection.

In still one more embodiment, beams of radiation are focused to an array of elongated spots on the surface at oblique angle(s) of incidence to the surface where the centers of the spots are arranged along a substantially straight line. Scattered radiation from the spots are imaged onto corresponding receivers or detectors in an array by means of imaging optics with a focal plane that substantially contains all of the spots.

In yet another embodiment, the same optics is used for focusing illumination beams of radiation to an array of spots on a surface and for imaging scattered radiation from the spots onto corresponding receivers or detectors in an array. The optics has an aperture where the illumination beams are focused through a first portion of the aperture and the imaging occurs through a second portion of the aperture. Preferably, the second portion is larger than the first portion, which enhances the sensitivity of detection.

It should be noted that any one or more features in the above-described embodiments may be employed in combination with one or more features of a different embodiment for enhanced performance.

BRIEF DESCRIPTION OF THE DRAWINGS

For simplicity in description, identical components are labeled by the same numerals in this application.

DETAILED DESCRIPTION OF THE EMBODIMENTS

The costs associated with dark-field pattern inspection has increased steadily with enhanced performance. As semiconductor fabrication approaches finer design rule and resolution, the complexity of inspection tasks has increased dramatically, which, in turn, increases the complexity and costs of the optical front end of the inspection tool and of detection electronics. Furthermore, the variety of situations calling for optical inspection means that a versatile optical inspection tool is preferably compact, rugged and has a small foot print so that it is less sensitive to vibrations, and integratable with semiconductor processing equipment. Preferably, the system can be used for inspecting surfaces with diffracting patterns thereon such as patterned wafers, as well as surfaces without such patterns such as unpatterned semiconductor wafers. The embodiments of this invention also enable faster and more sensitive inspection to be performed at a reasonable cost.

Figure 1:
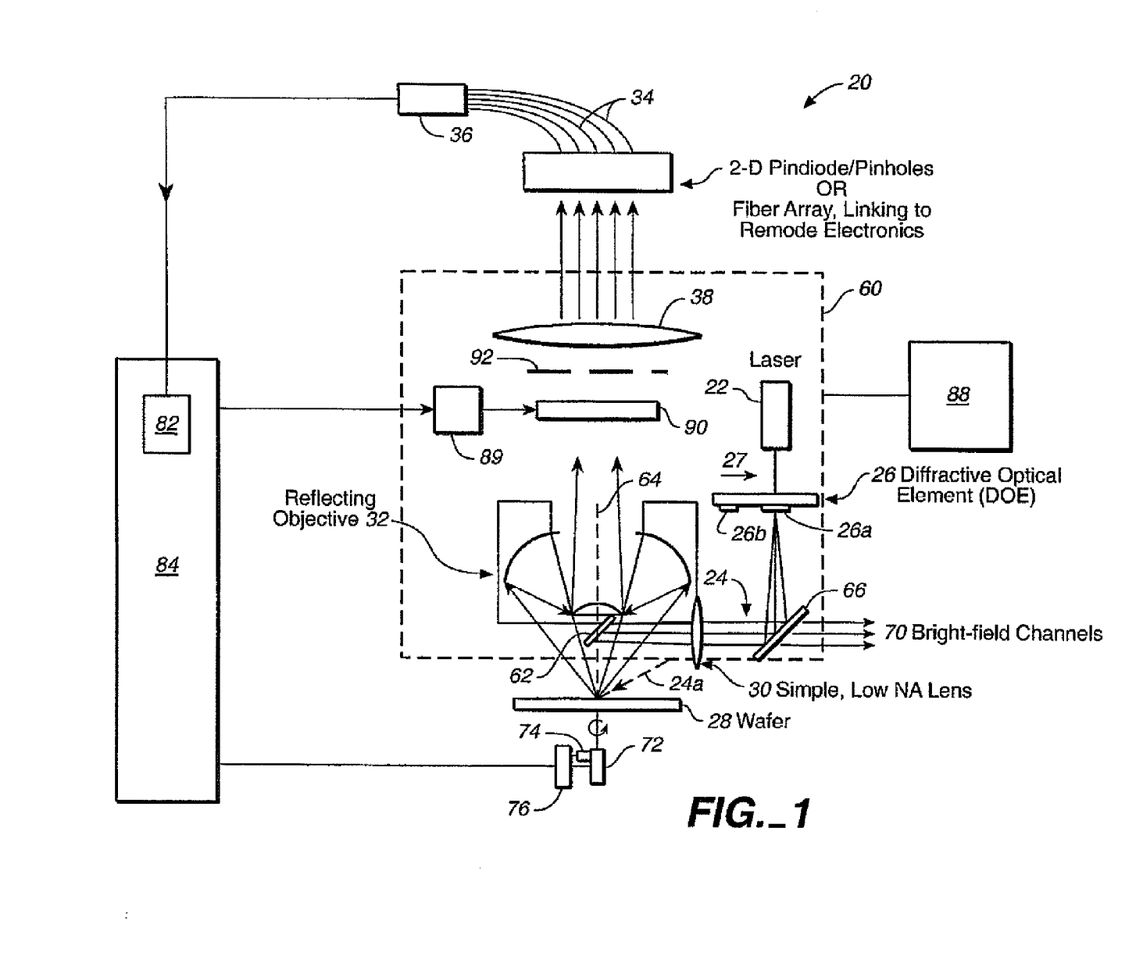
FIG. 1 is a schematic view of a multi-spot dark-field/bright-field inspection and imaging system to illustrate an embodiment of the invention.

The elements of the optical front-end design (such as those in an optical head) of the proposed system 20 are shown in FIG. 1. The radiation from a laser 22 is first split into an array 24 of beams, preferably a two-dimensional array, by the action of a diffractive optical element 26a on substrate 26. These beams are simultaneously focused onto the surface of a sample such as a semiconductor wafer 28, placed on a spinning stage, preferably a precision spinning stage, by a lens such as a simple doublet lens 30. Preferably lens 30 has a numerical aperture of not more than 0.8. The radiation scattered off each spot is collected by a reflecting objective 32, and imaged by an objective 38 onto a corresponding fiber in an M by N array 34 of optical fibers arranged to correspond to the distribution of the spots on the wafer. These fibers carry the radiation to an array 36 of avalanche photodiodes (APD), amplifiers, and digitizers. Other types of detectors are possible and may be used as described below. Alternatively, instead of imaging the scattered radiation collected from each spot on the wafer to an optical fiber, it may be imaged onto a detector in a detector array. In the embodiment of FIG. 1, the illumination beams 24 are directed towards the wafer surface in directions that are substantially normal to the surface of the wafer. Preferably the beams illuminate on the wafer surface spots that are substantially circular in shape.

Preferably, beams 24 reach sample 28 in directions substantially normal to the sample surface, and the collection or imaging optics comprising objectives 32, 38 are rotationally symmetric about a line 64 normal to the sample surface. As noted above, preferably the beams 24 illuminate on the wafer surface spots that are substantially circular in shape. In this manner, the illumination beams and the collection optics are rotationally symmetric about line 64. Then there is no need to keep track of the orientations of the illumination and collection optics relative to any diffraction or scattering patterns from the sample surface. Relative motion is caused between beams 24 and the sample surface so that preferably the beams trace or scan spiral paths on the sample surface, in a manner described below.

Figure 2:
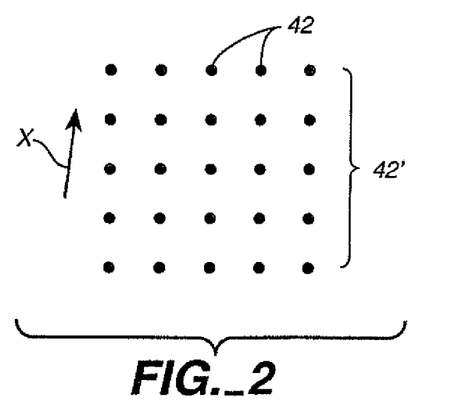
FIG. 2 is a schematic view of a two-dimensional arrangement of multiple illuminated spots on the surface inspected to illustrate the embodiment of FIG. 1.
Figure 3:
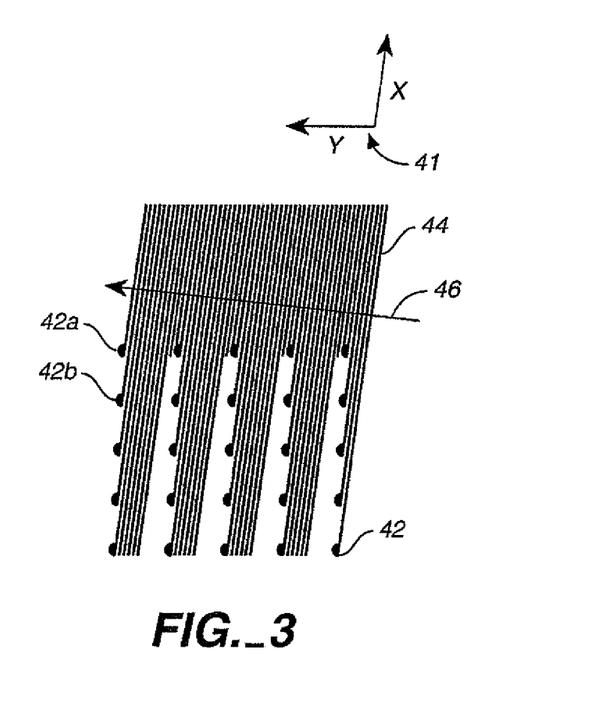
FIG. 3 is a schematic view of the multiple spots of FIG. 2 and their scan paths across the surface inspected to illustrate the embodiment of FIG. 1.
Figure 4:
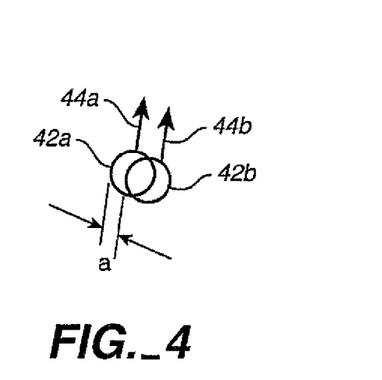
FIG. 4 is a schematic view illustrating the scan paths of two adjacent spots to illustrate the embodiment of FIG. 1.

The orientation of the spots 42 illuminated by the array 24 of beams is slightly rotated with respect to the tangential direction x of the wafer as the wafer is rotated as shown in FIG. 2. The spots along a given column "paint" adjacent paths as shown in FIG. 3. In a xy coordinate system 41, the thick arrow 46 illustrates the y direction of the image obtained. The separation between the adjacent spots is chosen so as to satisfy a desired sampling level (e.g. 3×3 or 4×4 samples per spot width). The detectors are sampled at uniform intervals in time at a rate of typically 3 or 4 samples per point spread function (PSF). This is illustrated in FIG. 4, which shows the paths of two adjacent spots, such as spots 42a and 42b in FIG. 2 travelling along paths 44a and 44b respectively. The two paths may be offset by a separation d substantially equal to one-third or one-quarter of the spot size to achieve the 3×3 or 4×4 samples per spot width, so that the spots 42a and 42b would overlap by two-thirds or three-quarters of the spot size. Thus, a one-dimensional scan of the wafer produces a two dimensional image, as illustrated in FIG. 3.

The optical components in the design are quite simple. The multi-beam splitter 26a may be one similar to the grating element used for a similar purpose in U.S. Pat. No. 6,208,411, where the element is a specially designed diffractive optical element. In choosing the total number of spots 42, it is desirable to pay attention to the total system complexity including, in particular, costs associated with the electronics. It has been determined that a total number of 128 channels is a reasonable compromise. This is achieved through a 16×8 array of spots. Other combinations are also possible. In some applications, the use of an odd number of spots such as 17×7 may be advantageous. The angular orientation of the spots with respect to the tangential direction of the wafer is chosen such that the spots in a column traverse the space between any two adjacent horizontally positioned spots (FIG. 2), resulting in a complete coverage of a swath of the wafer. In one embodiment, the separation between the spots is chosen such that 4 samples per point spread function (PSF) are attained in each direction. This is a slightly denser sampling than in the case of the AIT™ system available from KLA-Tencor Corporation of San Jose, Calif. The denser sampling reduces processing time, because smaller interpolation kernels are allowed for the same level of residual interpolator truncation error. The fact that the scan is spiral also favors a denser sampling, since the interpolation is inherently more complex than for a rectilinear scanner.

The intensity profiles of the spots are Gaussian shaped with a $1/e^2$ intensity width of 5 microns, for example. At a sampling level of 4×4 per spot width, the total width (i.e. swath width) of the tracks of the 128 (for a 16 by 8 array) spots is about 160 microns. In this context, a track is the locus of a spot as the sample is scanned. The maximum amount of the beam fan out in at the focusing lens 30 is so small that only a simple doublet suffices for focusing. Other types of lenses may also be used instead.

The dark-field collector in this design is a reflecting objective 32, placed directly above the illuminated field. While a 0.5 numerical aperture (NA) lens may be used for objective 32, lenses of other NA are possible. The reflecting lens performs two tasks: i) it collects the radiation scattered off each spot, and ii) it images the spots onto a corresponding array of fibers. The separation of the spots on the wafer is such that they can be considered as completely independent, without inter-spot interferences.

The radiation provided by laser 22 may contain one wavelength component or more than one wavelength component. Such radiation may include a wavelength component in the ultraviolet range, deep ultraviolet range, visible or infrared range, or wavelength components in more than one of the four different wavelength ranges. The laser or other radiation source 22 may operate in the visible, infrared, ultraviolet or deep ultraviolet range or ranges. An attraction of using a reflecting objective such as mirror 32 is that it functions well over a large range of wavelengths. For some applications, a refractive objective may also be used instead of a reflecting one for collecting and imaging scattered radiation from the wafer 28 to the fiber array 34.

Laser 22 may emit radiation of substantially a single wavelength in the system. Alternatively, laser 22 may emit radiation of a plurality of wavelengths, although radiation of only one of the plurality of wavelengths is used at any one time for inspection. The diffracting element 26a is preferably placed at the back focal plane of lens 30, so that the beams 24 are focused to the surface of the wafer 28, where the axes of beams 24 are substantially parallel to one another and perpendicular to the wafer surface, satisfying the condition of telecentricity.

Where radiation of a different wavelength is employed in scanning the sample surface (such as where laser 22 has more than one possible wavelength), the spot separation may change if the same element 26a is used to diffract the laser beam, since diffraction by element 26a is wavelength dependent. In such event, a different diffraction element such as element 26b may be used to compensate for the change in wavelength so that the spot separation remains substantially the same. Beam forming optics (not shown) may be used to change the width of the beam from the laser in order to maintain the same spot size as before, so that the collection optics in the system need not be changed. This switching between diffracting elements 26a and 26b can be accomplished readily by moving substrate along direction 27 using means such as a motor (not shown in FIG. 1). Since phase changes are not of interest and are not detected, there is no requirement to align precisely the element 26b with respect to the beam. Obviously more than two diffraction elements may be formed on the same substrate 26 in the event the laser beam contains more than two wavelength components.

Instead of changing the diffracting element when radiation of different wavelength is used, the same spot separation and spot size as before can be achieved by altering the focal length of the focusing lens 30 in FIG. 1. Then the collection optics also need not be changed. However, since the diffracting element is preferably placed at the back focal plane of lens 30, once the focal length of the lens is altered, the element needs to be moved to a new location which is again at the back focal plane of the lens 30. Where it is desirable to change the spot separation and spot size, one can alter the wavelength of the radiation used to inspect the wafer without changing the illumination optics. However, the imaging optics may then need to be altered by changing the magnification of the lens 38 so that lens 38 will still focus the collected radiation from the spots and image onto the fibers. To obtain a different spot separation and spot size without changing the wavelength of the radiation used to inspect the wafer, one can alter the focal length of lens 30, or alter the diffracting element and beam forming optics. Such and other variations are within the scope of the invention.

Where laser 22 emits more than one wavelength component, appropriate wavelength selection optical elements such as filters or beam splitters (not shown) may be employed in the path of the beam from laser 22 to select the component of the desired wavelength, so that radiation substantially at only one selected wavelength is supplied to element 26a or 26b at any one time. In such event, laser 22 and the wavelength selection optical elements form an optical source that supplies radiation of a selectable wavelength from a plurality of wavelengths. Obviously, other types of optical source that supplies radiation of a selectable wavelength may be used instead. Thus, alternatively, where laser 22 emits monochromatic radiation, a different laser emitting radiation of a wavelength different from that emitted by laser 22 may be employed to replace laser 22. As another alternative, separate monochromatic or polychromatic lasers may be combined by means such as dichroic filters to provide radiation of selectable wavelength. Such and other variations are within the scope of the invention.

In a system for enhanced detection sensitivity, it is desirable for the collection optics such as objective 32 to have a large numerical aperture (NA) whereas for the illumination optics such as lens 30, a low NA will be sufficient. System 20 illustrated in FIG. 1 shows a particularly compact design where the illumination optics and collection optics employ different objectives, that is objectives 30 and 32, where the collection objective 32 has a larger NA than that of the illumination objective 30. By using low NA illumination optics, it is possible for both the illumination optics and collection optics to fit within the space close to the wafer 28 in a particularly compact design of the optical head, as shown in FIG. 1.

Thus, according to another aspect of the invention, the optical head in the embodiment of FIG. 1 is compact and has a particularly small footprint. Thus, optical head 60 within the dotted line box includes a laser 22, diffractive elements 26a and 26b, lens 30, collection objective 32, and the array of optical fibers 34. In a slightly modified embodiment than that shown in FIG. 1, laser 22 may also be located outside the optical head 60 and may be placed so that its output laser beam is directed to the diffractive element 26a in the optical head 60, possibly by means of an optical fiber link. Such and other variations are within the scope of the invention.

The combination of the collection objective 32 and objective 38 focuses radiation scattered from each illuminated spot 42 on the surface of wafer 28 to a corresponding optical fiber in the optical fiber array 34. Scattered or reflected radiation from each spot is then carried by its corresponding fiber to a detector which may be an avalanche photodiode, a pin photodiode, a photomultiplier, or other individual detector. The detector may be part of an array 36 of detectors. By using an optical fiber array 34, the detectors 36 do not need to be included in the optical head 60 and can be located at a distance from the optical head, thereby further reducing the size of the optical head. Alternatively, for applications where spatial considerations are not as important, the optical fiber array 34 may be omitted and the scattered radiation from each spot may be focused directly by objective 32 to a corresponding detector in the detector array 36 within the optical head. Such and other variations are within the scope of the invention.

Figure 9:
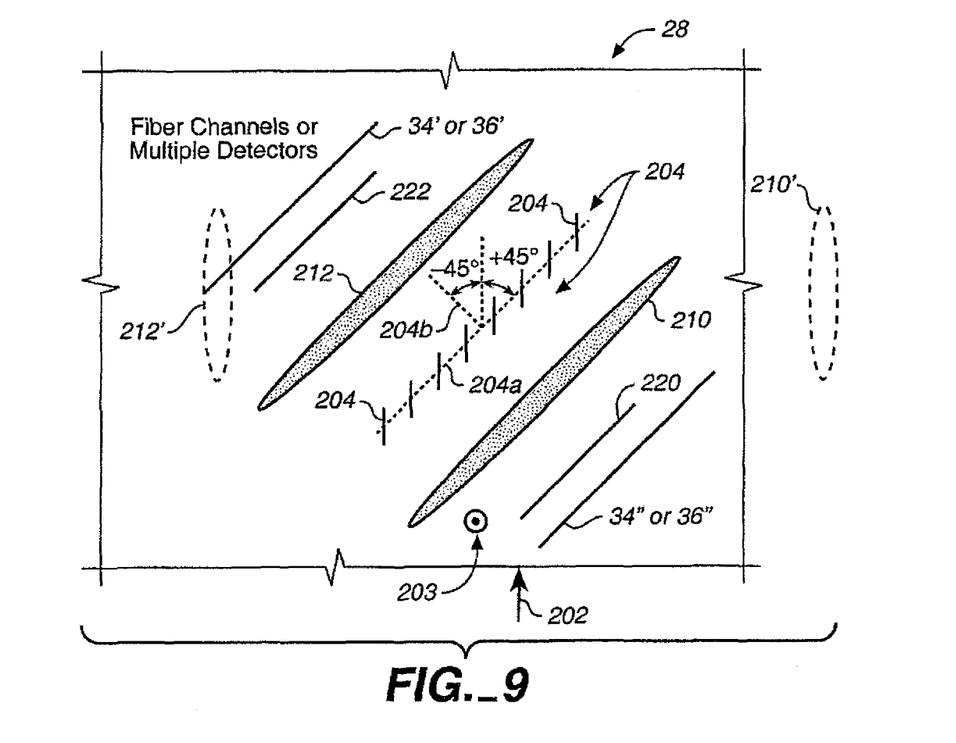
FIG. 9 is a top schematic view of an optical inspection and imaging system to illustrate yet another embodiment of the invention.

In the above description, element 26a diffracts the laser beam from laser 22 into a two-dimensional array of beams 24. Instead of diffracting the laser beam into a two-dimensional array of beams, element 26a may instead diffract the beam into a one-dimensional array of beams to illuminate a one-dimensional array of illuminated spots on the surface of the wafer 28. Such one-dimensional array of illuminated spots may, for example, comprise the five illuminated spots appearing as the right most column 42' in FIG. 2. Another example of such one-dimensional array of beams and spots is illustrated in FIG. 9. The paths of illuminated spots in column 42' may also overlap as indicated in FIG. 4. Such and other variations are within the scope of the invention.

Bright Field Detection

Bright field detection is where specularly reflected radiation is detected, such as that described in S. Stokowski and M. Vaez-Iravani, "Wafer Inspection Technology Challenges for ULSI Technology", Proceedings of conference on Characterization and Metrology for ULSI Technology, Edited by D. G. Seiler, A. C. Diebold, W. M. Bullis, T. J. Shaffner, R. McDonald, and E. J. Walters, American Institute of Physics, PP. 405-415 (1998).

In the embodiment of FIG. 1, the array of illumination beams 24 are focused by lens 30 to a mirror 62 which reflects the beams towards wafer 28. Mirror 62 also acts as an aperture stop to reduce or prevent specular reflection of the beams from the surface 28 from reaching the optical fiber array 34, so that the collection mirror 32 collects only radiation scattered by the spots along collection paths that are away from the specular reflection direction in a dark field imaging system. Dark field systems are those where the radiation collected and detected is that scattered by the sample and collected along collection paths that are away from the specular reflection direction from the sample surface of the illumination beams. Dark field systems are explained in more detail in the above-referenced article by S. Stokowski and M. Vaez-Iravani.

FIG. 1 also shows the reflected path into the "bright-field" channels 70, which may comprise an optical fiber array similar to array 34. The beams 24 from element 26a are first reflected by a beam splitter 66 towards lens 30 and mirror 62. Part of the radiation specularly reflected by the wafer surface is again reflected by mirror 62, collimated by lens 30 and passes through the beam splitter 66 towards bright-field channels 70 and then to an array of detectors (not shown). As in the case of dark field detection, the radiation reflected from each spot is imaged by lens 30 onto a corresponding channel in channels 70 and then to a corresponding detector. Also as in the dark field system, the detector array in the bright field system need not be included in optical head 60 for compactness. Where space is not as much a concern, channels 70 may be replaced by an array of detectors so that lens 30 and simple optics (not shown) located downstream from lens 30 in the same optical path image radiation reflected by each spot directly to the corresponding detector in the detector array. Bright field detection is useful for detecting parameters such as reflectivity, contrast, and features such as areal shallow defects.

The bright-field channels may yield useful information on large defects that can be discerned by detecting the reflectance at various spots on the surface of wafer 28. If bright-field inspection at the proposed resolution is found to be useful, then the appropriate fiber channels can be set up in exactly the same manner as those in the case of the dark-field channels, where a detector array in addition to array 36 is employed for bright field detection. Bright-field and dark-field radiation could also be detected sequentially using the same electronics. Alternatively, they may be used simultaneously using separate electronics.

Wafer Scanning

Wafer 28 is supported on a chuck (not shown) which is rotated by means of a motor 72 and translated in a direction by gear 74 so that the illuminated spots 42 are caused to move and trace a spiral swath on the surface of wafer 28 to inspect the entire surface of the wafer. Both vacuum handling and edge handling of the samples are possible. Motor 72 and gear 74 are controlled by controller 76 in a mariner known to those skilled in the art. Thus, in the preferred embodiment, the optical head 60 remains stationary and the scanning of the beams 24 across the surface of the wafer 28 is accomplished by using motor 72, gear 74 and controller 76 to move the wafer so that the entire surface of the wafer is scanned. Alternatively, the optical head 60 may be caused to move in a manner known to those skilled in the art to trace the spiral path or another type of scan path for scanning wafer 28. The wafer may also be scanned along substantially linear zigzag paths using XY stages.

As noted above, the detector in array 36 may be a photodiode such as an avalanche photodiode; alternatively, it may be a photomultiplier tube. The output of each detector in the detector array 36 is supplied to processing circuit 82 where the circuit may comprise a microprocessor, hardware logic or programmable logic circuits, such as those using FPGA's or dynamic logic or various combinations of these elements. Circuit 82 may be a part of or connected to a computer 84 that is in communication with controller 76, so that scattered radiation from a particular detector in array 36 can be matched with a location on the surface of the wafer 28. Where processing circuit 82 is a microprocessor, it can be a co-processor within computer 84. Processing circuit 82 performs certain initial processing of the signals, such as signal amplification and conversion from analog-to-digital form. It may pass the digital signals to computer 84 to perform further processing such as die-to-die comparison, or it may perform some or all such further processing itself.

One aspect of the design in system 20 of FIG. 1 is that it is based on a stationary optics as described above, and spinning of the wafer as described above, in a manner similar to that in the SP1™ tool, also available from KLA-Tencor Corporation of San Jose, Calif. It is preferable for system 20 to have a rather precise spinning action. For example, the spinner is capable of some +/−15 microns stability in height, and uniform spinning on the micron scale.

This performance can be achieved by means of an air bearing stage, for example. By scanning the wafer surface with multiple spots simultaneously, the scanning of the entire wafer surface can be performed in shorter time than if a single spot were used.

An important consideration that pertains to this spiral scanning action is that it begins to deviate from very closely linear motion as the position of the beams approaches the center of the wafer. However, it should also be remembered that at any given time, one has a precise (within a pixel) knowledge of the position of any of the beams, which allows one to correct for such scan deviations.

Filters for Reducing Diffraction from Manhattan Geometry and from Pattern

At any given position on the wafer 28 during the beam scanning and inspection process, each of the spots 42 illuminates a number of shapes, which primarily lie along the Manhattan geometry. These shapes all generate a two dimensional Sine function, but with different phases, giving rise to a "+" speckle pattern. As the wafer rotates, this pattern also rotates. If one were to detect all the available scattered radiation from the wafer, one would also receive parts of this diffraction pattern. In the ensuing die-to-die comparison, the presence of this large background would possibly result in significant errors.

Figure 5:
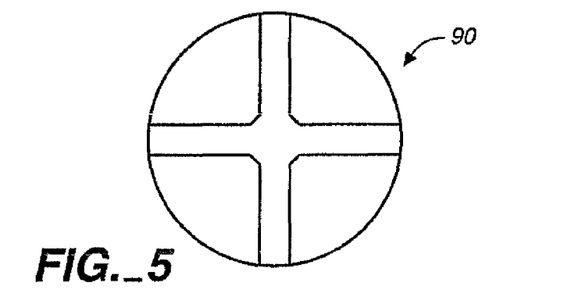
FIG. 5 is a schematic view of a spatial filter in the collection path of the embodiment of FIG. 1 to further illustrate the embodiment.

In rectilinear scans, one could resolve these problems by means of a stationary spatial filter to filter out the speckle pattern and placing the detectors along the 45 degrees lines with respect to the horizontal-vertical directions. In system 20, the rotation of the wafer 28 results in a rotating diffraction pattern. This pattern can be eliminated or reduced by placing a "+" shaped filter 90 (i.e. a filter having an aperture that passes radiation except for a "+" shaped area), shown more clearly in FIG. 5, directly above the illuminated field, in the path of the radiation after emergence from the reflective objective 32. This filter 90 is made to rotate by means of a motor 89 in FIG. 1 under the control of computer 84 in unison with respect to the rotation of wafer 28 under the control of controller 76, resulting in a continuous obstruction of the diffracted light. Possible approaches to this issue include the use of ball-bearing based systems, which can be mounted directly at the exit port of the reflecting objective. The use of a programmable liquid crystal filter having an aperture that is changed in synchronism with the rotational motion of the sample surface under the control of computer 84 to implement filter 90 instead of a mechanically rotated one as described above may be viable for low rotation rates of the wafer.

Figure 6:
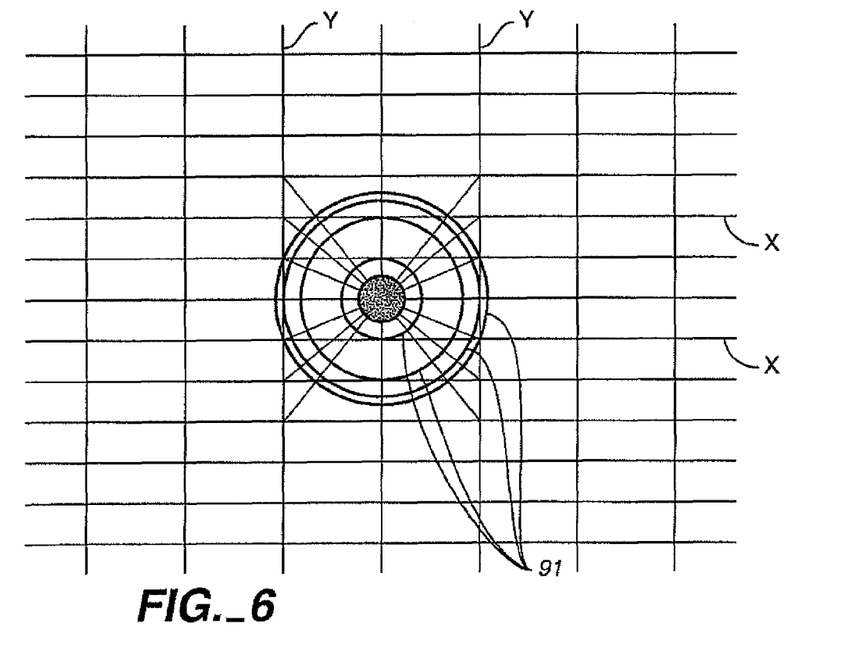
FIG. 6 is a schematic view of an annular-shaped spatial filter that may be used in the in the collection path of the embodiment of FIG. 1 to illustrate the invention.

In addition to diffraction from the Manhattan Geometry, the presence of any periodic structures such as arrays in DRAMs on the surface of the wafer may also give rise to a two-dimensional Fourier components when illuminated with normal incidence radiation. If the directions of the expected pattern scatter from the surface are known, spatial filters may be designed to block such scattering, thereby detecting only the scatter by anomalies on the surface. FIG. 6 is a schematic view illustrating the two-dimensional Fourier components of an array structure that is periodic in the X and Y directions when illuminated with normal incidence radiation. As the sample rotates, all of the spots at the intersections of the X-Y lines will rotate, thereby generating circles 91. These circles represent the loci of the Fourier components as the wafer is rotated. The dark opaque circle at the center is the blockage of the collection space caused by stop 62 in FIG. 1.

From FIG. 6, it is noted that there are gaps in between the circles where there are no Fourier components. At least in theory, it is possible to construct a programmable filter (e.g. a liquid crystal filter) in which annular bands of arbitrary radii are blocked out. A simple spatial filter may be constructed also to achieve many of the objectives herein. Thus, if the cell size of a regular memory array on the wafer is such that its X and Y dimensions are not larger than about 3.5 microns, for example, this means that for 488 nanometers wavelength radiation used in the illumination beams 24, the first Fourier component is at about 8° to the normal direction 36. Therefore, if a spatial filter such as 92 of FIG. 1 is employed, blocking all collected radiation in the narrow channel that is at 8° or more to the normal direction 36 will leave an annular gap of 2 or 3° ranging from the rim of the central obscuration (i.e. 5 or 6°) to the rim of the variable aperture at about 8°. Under these conditions, as the wafer spins, no Fourier components can possibly get through the annual gap and scatter from the array is suppressed. In one embodiment, the spatial filter 92 in FIG. 1 used leaves an annular gap between about 5 to 9° from the normal direction 64 to the surface 28 of the wafer in FIG. 1. For DRAM structures of smaller cell sizes, such annular aperture type spatial filter may not even be necessary. While both filters 90 and 92 are employed in the embodiment of FIG. 1, it will be understood that for certain applications, the use of only one of the two filters may be adequate and is within the scope of the invention.

It will be noted that even though the collection objective 32 focuses radiation scattered from an array of spots 42, such scattered radiation from the spots are focused towards the optical fiber array 34 through a small area at the focal plane of the objective, so that by placing filter 90 and/or filter 92 at or close to the focal plane, the above-described effects can be achieved with respect to the scattered radiation from all of the illuminated spots 42 in the array of spots.

Detection Channels

Individual APD's, or one or more arrays of APD's, may be used as detectors in array 36 for each of the dark-field channels. These detectors provide close to photon noise limited performance for typical illumination levels. Pin diodes, or one or more arrays of pin-diodes may be used if bright-field channels are considered important, then a separate APD board may be provided for those, or an array of PIN diodes.

In the preferred embodiment, each APD channel has its own settable supply, preamplifier, and analog-to-digital converter (ADC), which can be operated at up to 60 MHz. That is, the potential of this system in terms of data rate approaches 5-10 GHz, even though a practical data rate may be somewhat lower. It is important to note that the detection electronics part of the design in this case may be completely separate from the front-end optics, such as the optical head 60, which necessarily results in a compact optical head. The optical head may be readily integrated into semiconductor processing equipment 88, so that it is more convenient for anomalies on the wafer surface to be detected during processing or between processing steps by means of semiconductor processing equipment 88.

Processing Circuit 82

Preferably the detected signals are directed into a massive bank of random access memory (RAM) in circuit 82, capable of holding up to 85 Gbytes of data. As the wafer is scanned the data are gathered from the various dice at different locations on the wafer. Subsequent image processing is primarily based on a die-to-die comparison process, applied to side-by-side dice, in a rectilinear direction, much in the same way as that in conventional systems, such as the AIT™ systems available from KLA-Tencor Corporation of San Jose, Calif.

Because of the fact that the scanning is performed in a spiral rather than rectilinear fashion, the die-die comparison may be performed on a stored version of the 12-bit gray scale data. To achieve this, it will not be necessary to store the data from the entire wafer, rather only a sufficient amount to enable die-die on the present location. Nevertheless, for some applications, it may be desirable to provide sufficient memory to store an entire wafer map. At a pixel size of 1.25×1.25 microns, a 300 mm wafer has approximately 45 gigapixels. To store all pixels as 12-bit values, some 70 GB of memory is preferred. The processing power required must be sufficient to keep up with the pixel rate. A typical pixel rate for some embodiments can be about 1 Gpixels/sec. Higher speeds are also possible.

In one embodiment where the scanning is non-rectilinear, it may not be possible simply to retain the image data for a single swath in order to do die-to-die comparison, as the AIT and other rectilinear scanning die-to-die machines do. However, by retaining all pixel information on more than one swath revolution of data on the wafer as it comes in, and by concurrently comparing incoming pixels with those of a reference die which is chosen so that its pixels are acquired a little sooner, each die can be compared with a reference die during the wafer scan; when the spiral scan is complete, the processing will be nearly finished.

Figure 7:
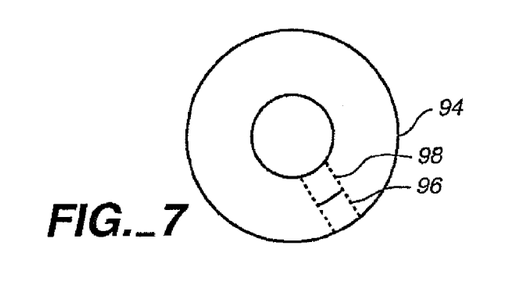
FIG. 7 is a schematic view of an annular-shaped illuminated region of the surface inspected containing two dice to illustrate one aspect of the invention in the embodiment of FIG. 1.

As noted above, a reference die may be chosen so that its pixels are acquired a little sooner, so that each die can be compared with a reference die during the wafer scan. This is illustrated in FIG. 7 which is a schematic illustration of data obtained from an annular region 94 of the wafer. The wafer may be scanned beginning at a point on or near the circumference of the wafer, or at or near the center of the wafer. Assuming that the spiral path scan of the array of spots 42 starts out at the circumference of the wafer and spirals in towards the center of the wafer during the scanning, a reference die 96 may be defined at or close to the outer circumference of the annular region 94. Therefore, when the data from the target die 98 is obtained, such data may be compared to the data in the reference die obtained earlier for anomaly detection. Obviously, die-to-die comparison using dice data acquired earlier from a reference die different from die 96 may be used instead and is within the scope of the invention.

Figure 8:
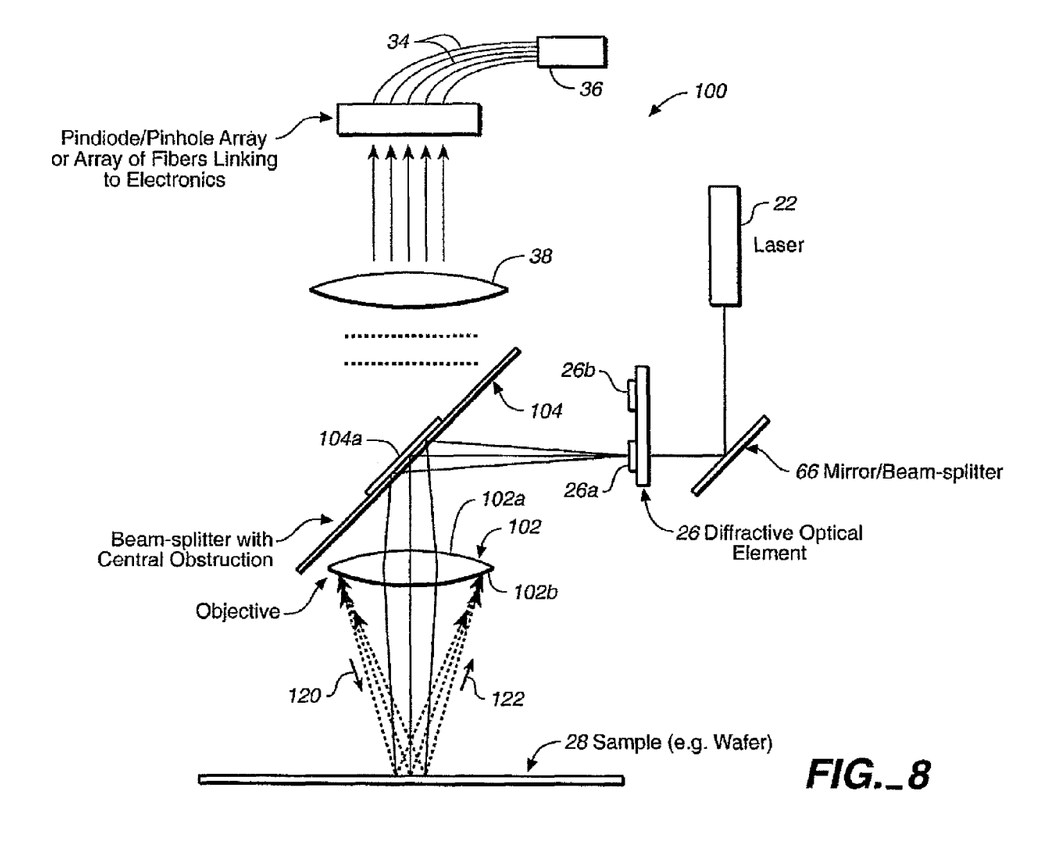
FIG. 8 is a schematic view of an optical inspection and imaging system to illustrate another embodiment of the invention.

FIG. 8 is a schematic diagram of an optical inspection and imaging system illustrating an alternative embodiment of the invention. Instead of using two separate objectives, one for illumination and the other for collection, the embodiment 100 of FIG. 8 employs a single objective for this purpose, although different portions of the objective 102 may be employed for illumination and for collection. Thus, as shown in FIG. 8, a laser beam from laser 22 is reflected by a mirror or beamsplitter 66 and is diffracted into an array of beams 24 by means of diffractive element 26a. Beams 24 are reflected by a center reflective portion 104a of beamsplitter 104 to lens 102. In the preferred embodiment, beams 24 are focused by a center portion 102a of the aperture of lens 102 to the surface of wafer 28. Scattered radiation from the illuminated spots 42 are collected by lens 102 and directed towards the beamsplitter 104. The center reflective portion 104a acts as an aperture stop that prevents specular reflection from the surface of the wafer from reaching the optical fiber array 34. Thus, only the scattered radiation collected by the circumferential portion 102b of the aperture of lens 102 can pass through the beamsplitter 104 and focused by lens 38 towards the detector or optical fiber array 34. Preferably, the portion 102b for collecting scattered radiation is larger than the portion 102a used for illumination, which enhances the sensitivity of detection.

To simplify FIG. 8, the components shown in FIG. 1 for moving the wafer, the bright field channels, the processing circuit and computer have been omitted from the figure. The embodiment of FIG. 8 has the advantage that it is even more compact compared to the embodiment of FIG. 1, since a single objective is used for both illumination and collection. Instead of using a lens as shown in FIG. 8, it may also be possible to use a reflecting objective to ensure easy operation and a large wavelength range. Instead of using a center portion 102a for focusing the illumination beams and a circumferential portion 102b for collecting the scattered radiation, the arrangement in FIG. 8 can also be modified by directing the illumination beams 24 through a side portion of the objective, such as the left side of the objective 102 and using the other side, such as the right side, for collection of the scattered radiation. Such and other variations are within the scope of the invention. It will be noted that where the paths of illumination beams are at oblique angles to the surface of sample 28, at least one dimension of the illuminated spots may be such that it is not less than about 5 microns. Similar considerations to those described above also apply to the bright-field channels in the embodiment of FIG. 8 (not shown in FIG. 8) similar to channels 70 of FIG. 1. However, in this case the signal generated in each bright-field channel is due to the light reflected off each of the spots.

In the embodiment of FIG. 1 described above, the illumination beams 24 are directed towards the wafer surface in directions that are substantially normal to the surface of the wafer. This is not required, however. Thus, for some applications, the illumination beams may be directed towards a wafer surface at an oblique angle such as along the paths 24a indicated by the dotted line in FIG. 1, so that at least one dimension of the illuminated spots is not less than about 5 microns. Thus, especially for the inspection of unpatterned surfaces such as unpatterned wafers, illuminating the wafer surface at an oblique angle may be desirable for some applications. The same applies to the embodiment of FIG. 8.

FIG. 9 is a top schematic view of an optical inspection and imaging system to illustrate yet another embodiment of the invention. As shown in FIG. 9, a single line of illumination beams is supplied at an oblique angle along direction 202 to the surface of a wafer 28, only a portion of which is shown in FIG. 9. The single line of illumination beams (not shown) illuminate a single file of elongated illuminated spots 204 on the surface of the wafer. Preferably, the beamsplitter (not shown in FIG. 9) that is used to generate the single file of illumination beams is oriented at or near an angle, such as 45° for example, relative to the plane of incidence of the illumination beams, so that the line 204a connecting the centers of the spots 204 is also at or near 45° with respect to the plane of incidence. In this context, the plane of incidence is defined by a plane containing the illumination direction 202 and a line 203 (pointing out of the plane of the paper) intersecting direction 202 and normal to the surface of the wafer 28. Thus, if direction 202 is regarded as an axis of a coordinate system, the line 204a connecting the centers of the spots 204 is substantially at +45° to such axis.

Radiation scattered from the spots 204 are collected along directions substantially perpendicular to line 204a by objectives 210 and 212 located above the plane of the surface inspected and on opposite sides of line 204a. Objective 212 images the scattered radiation from each spot 204 onto a corresponding forward channel or detector in the optical fiber array 34' or detector array 36'. Similarly, objective 210 images the scattered radiation from each spot 204 to its corresponding backscatter fiber or detector in the fiber optic array 34' or detector array 36". It will be noted that objectives 210 and 212 may be situated so that all of the spots 204 are substantially within their focal planes. As shown in FIG. 9, objective 212 will collect the forward scattered radiation and objective 210 will collect the back scattered radiation. Instead of using lenses as shown in FIG. 9. objectives 210 and 212 may also be reflective objectives.

Alternatively, the beamsplitter that is used to generate the single file of illumination beams may be oriented at −45° with respect to the plane of incidence so that the spots (not shown in FIG. 9) would form a single file oriented at −45° to direction 202, and line 204b connecting the centers of the spots at such new locations is also at substantially −45° with respect to the plane of incidence.

If the beamsplitter for generating the array of illumination beams are oriented at −45° with respect to the plane of incidence, then the collection objectives 210 and 212 would also need to be rotated by 90° so that the spots 204 arranged with their centers along the line 204b would again be within their focal planes and that these objectives would again collect radiation scattered in directions substantially perpendicular to the line 204b.

Figure 10:
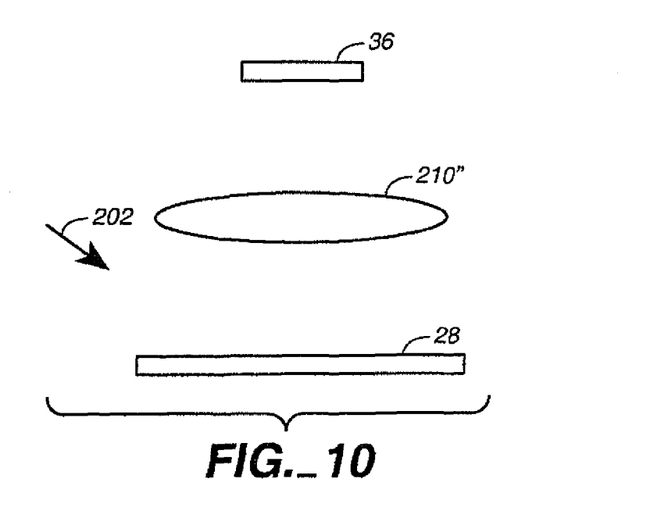
FIG. 10 is a schematic side view of an optical inspection and imaging system to illustrate still another embodiment of the invention in a single dark field configuration.

Instead of collecting and imaging scattered radiation in directions perpendicular to the line joining the centers of the illuminated spots 204 as described above, it is also possible to collect and image the scatter radiation in a double dark field configuration. In such configuration, the two objectives would be at locations indicated in dotted lines 210' and 212' where scattered radiation is collected substantially at +90 and −90 degrees azimuthal angle relative to the illumination beams as they reach the surface; the fiber channels or detectors have been omitted in such configuration to simplify the figure. In a double dark field configuration, different spots along the line 204a or 204b will be located at different distances from the objectives so that at least some of them will be out of focus. Even though some of the spots 204 will be out of focus or somewhat out of focus, this may not have significant adverse effects on some applications, such as unpatterned surface inspection. Obviously only one of the two objectives 210 and 212 (or 210' and 212') may suffice for some applications, so that one of them can be omitted. It is also possible to place collection optics 210" and a detector array 36 or a collection of individual detectors (not shown) directly above the area of the surface of sample (and therefore in the plane of incidence of beams along direction 202) inspected in a single dark field configuration to detect surface anomalies, such as in the configuration shown in FIG. 10. When the collection optics 210" is in such position, it images to the detector array or detector collection the scattered radiation in at least one direction that is substantially normal to the surface. Preferably the collection optics 210" used has a large numerical aperture for increased sensitivity.

If the illumination beams are polarized, it may be desirable to insert a polarizer between each of the two objectives 210 and 210' and their corresponding fiber or detection channels. Thus, in the presence of a dielectric material such as silicon oxide, circularly polarized radiation in the illumination beam may be preferable. The presence of small defects may cause P-polarized radiation to be more efficiently scattered. If S-polarized radiation is employed in the illumination beams, scattering caused by the presence of roughness on the surface can be further suppressed if only S-polarized light is collected. For this purpose polarizers may be placed in the paths of beams 24 and polarizers 220 and 222 may be placed in the collection path for enabling the detection of polarized radiation components, which may in turn indicate the type of anomalies present on the wafer. Corresponding polarizers may be placed along the collection paths in the double dark field embodiments. Instead of using refractive objectives such as lenses 210, 210', 212, 212', reflective objectives may be used which can be used for collection over a large wavelength range.

While the invention has been described above by reference to various embodiments, it will be understood that changes and modifications may be made without departing from the scope of the invention, which is to be defined only by the appended claims and their equivalents. For example, while the embodiments are illustrated with respect to wafer anomaly detection, the invention may be used for anomaly detection on other types of surfaces as well, such as flat panel displays, magnetic and optical heads, disks and so on. All of the references referred to above are incorporated herein by reference in their entirety.

What is claimed is:

1. A method for detecting anomalies of a surface, comprising:
   focusing illumination beams of radiation to an array of spots on the surface in directions that are oblique to the surface;
   imaging radiation scattered from said spots onto a first array of receivers or detectors in a dark field imaging scheme so that each receiver or detector in the first array receives radiation that is forward scattered from a corresponding spot in the array of spots in a direction that is a same direction as the illumination beams of radiation; and
   imaging scattered radiation from said spots onto a second array of receivers or detectors different from the first array in a dark field imaging scheme so that each receiver or detector in the second array receives radiation that is back scattered from a corresponding spot in a direction that is opposite a direction of the illumination beams of radiation.

2. The method of claim 1, wherein said scattered radiation from said spots is imaged in the dark field imaging scheme onto the first array by means of reflective optics.

3. The method of claim 1, further comprising selecting a wavelength and supplying the illumination beams of radiation so that the radiation comprises a component of the selected wavelength in a UV, deep UV, visible or infrared wavelength range, said supplying comprising passing a beam of radiation of the selected wavelength component through a diffracting element to form the illumination beams.

4. The method of claim 1, wherein the focusing focuses the beams to an array of elongated spots, said spots arranged along a substantially straight line.

5. The method of claim 4, further comprising causing rotational motion of the surface while leaving the beams at substantially stationary positions.

6. The method of claim 4, wherein the straight line is at an angle of 45 degrees to a plane of incidence of the beams.

7. The method of claim 6, wherein said imaging images the scattered radiation to the first or second arrays of receivers or detectors along one or more directions that are substantially normal to the straight line.

8. The method of claim 1, wherein the scattered radiation from said spots is imaged by means of reflective optics onto the first and second arrays.

9. An apparatus for detecting anomalies of a surface, comprising:

illumination optics for focusing illumination beams of radiation to an array of spots on the surface in directions that are oblique to the surface;

first dark field imaging optics for imaging radiation scattered from said spots onto a first array of receivers or detectors so that each receiver in the first array receives radiation that is forward scattered from a corresponding spot in the array of spots; and second dark field imaging optics for imaging scattered radiation from said spots onto a second array of receivers or detectors different from the first array so that each receiver or detector in the second array receives radiation from that is back scattered from a corresponding spot.

10. The apparatus of claim 9, further comprising means for supplying a beam of radiation of a selected wavelength in a UV, deep UV, visible or infrared wavelength range, and a diffracting element that diffracts the beam of radiation of the selected wavelength component to form the illumination beams.

11. The apparatus of claim 9, wherein the illumination optics are further arranged to focus the beams to an array of elongated spots, said spots arranged along a substantially straight line.

12. The apparatus of claim 11, herein the straight line is at an angle of 45 degrees to a plane of incidence of the beams.

13. The apparatus of claim 11, wherein the first or second dark field imaging optics is further arranged for imaging the scattered radiation to the first or second arrays of receivers or detectors along one or more directions that are substantially normal to the straight line.

14. The apparatus of claim 9, wherein the illumination optics are further arranged to focus the beams to a one dimensional array of spots, said apparatus further comprising an instrument for causing rotational motion between the surface and the beams, wherein the instrument is operable to cause rotational motion of the surface while leaving the beams at substantially stationary positions.

15. The apparatus of claim 9, wherein the first dark field imaging optics includes reflective optics.

16. The method of claim 1, wherein:

wherein the array of spots is arranged along a substantially straight line and scanned perpendicular to such straight line, imaging scattered radiation from said spots onto the first array of receivers or detectors is accomplished by each receiver or detector in the first array receiving radiation that is forward scattered from a first direction that is substantially perpendicular to the straight line, imaging scattered radiation from said spots onto the second array of receivers or detectors is accomplished by each receiver or detector in the second array receiving radiation that is back scattered from a second direction that is substantially perpendicular to the straight line, and the first and second directions are on opposite sides of the straight line.

17. The apparatus of claim 9, wherein:

wherein the array of spots is arranged along a substantially straight line and to scan perpendicular to such straight line, the first dark field imaging optics are further arranged for imaging scattered radiation from said spots onto the first array of receivers or detectors by each receiver or detector in the first array receiving radiation that is forward scattered from a first direction that is substantially perpendicular to the straight line, the second dark field imaging optics are further arranged imaging scattered radiation from said spots onto the second array of receivers or detectors by each receiver or detector in the second array receiving radiation that is back scattered from a second direction that is substantially perpendicular to the straight line, and the first and second directions are on opposite sides of the straight line.

* * * * *

UNITED STATES PATENT AND TRADEMARK OFFICE
CERTIFICATE OF CORRECTION

PATENT NO. : 9,568,435 B2
APPLICATION NO. : 14/465656
DATED : February 14, 2017
INVENTOR(S) : Mehdi Vaez-Iravani et al.

Page 1 of 1

It is certified that error appears in the above-identified patent and that said Letters Patent is hereby corrected as shown below:

Column 1, Line 16, Cross Reference to Related Applications after "...filed Nov. 15, 2002.", add the following:

Application No. 10/418,352 also claims the benefit of Provisional Application No. 60/426,577, filed November 15, 2002.

Signed and Sealed this
Sixteenth Day of May, 2017

Michelle K. Lee
*Director of the United States Patent and Trademark Office*